United States Patent [19]
Augeri

[11] 4,318,235
[45] Mar. 9, 1982

[54] LABEL AND LABELLED ARTICLE

[75] Inventor: Joseph L. Augeri, Stamford, Conn.
[73] Assignee: The Nestle Co., Inc., White Plains, N.Y.

[21] Appl. No.: 157,847
[22] Filed: Jun. 9, 1980
[51] Int. Cl.[3] .......... G04F 3/00; G04F 3/02; A61F 13/02; B65D 3/26
[52] U.S. Cl. .......... 40/306; 40/2.2; 40/310; 428/43; 206/605; 206/608
[58] Field of Search .......... 428/915, 43; 206/604, 206/605, 606, 608, 609, 615; 40/2 R, 21 R, 21 B, 306, 310, 312, 159, 594, 2.2, 2 G, 306; 156/201, DIG. 10, DIG. 11, DIG. 12, DIG. 13

[56] References Cited

U.S. PATENT DOCUMENTS 2,053,726 9/1936 Marshall .......... 206/608
2,105,367 1/1938 Parsons .......... 206/604
2,420,045 5/1947 Krug .......... 40/306
2,864,547 12/1958 Guyer .......... 206/609
3,199,769 8/1965 Hillman et al. .......... 206/604
3,302,855 2/1967 Becker .......... 206/615
3,835,564 9/1974 Gottschalk .......... 40/306

FOREIGN PATENT DOCUMENTS 883700 6/1953 Fed. Rep. of Germany .......... 40/310
1174637 7/1964 Fed. Rep. of Germany .......... 206/605
6398 of 1899 United Kingdom .......... 40/306

*Primary Examiner*—Edward C. Kimlin
*Assistant Examiner*—L. Falasco
*Attorney, Agent, or Firm*—Vogt & O'Donnell

[57] ABSTRACT

A sheet-like label having a pattern of tear lines which define a panel and an elongated strip which is contiguous with a first edge of the label. One end of the strip can be manually engaged and the strip can then be pulled away from the remainder of the label to free the first edge of the panel. The panel can then be manually engaged at its first edge and the panel can thus be readily separated from the remainder of the label. The remainder of the label completely surrounds the panel and the strip so that after removal of the panel and the strip the edges of the label will remain continuous. The labelled article includes a label mounted to the body of the article so that the label closely overlies a surface of the body.

10 Claims, 6 Drawing Figures

LABEL AND LABELLED ARTICLE

BACKGROUND OF THE INVENTION

The present invention relates to packaging, and more particularly relates to a label having a removable panel and to an article to which such label is fixed.

In the packaging art, it has long been known to provide sheet like labels with removable panels defined by "tear lines". As used herein "tear line" is intended to include any narrow, linearly extensive feature of a sheet like label which is weaker than adjacent portions of the label so that the label may readily be torn along the feature. One form of tear line consists of a linearly extensive row of spaced perforations in the label.

Prior to the present invention it has been difficult to provide a panel which can readily and neatly be removed by hand from a label which closely overlies a surface of the body to which the label has been applied. It has been particularly difficult to fashion a label from which the panel can be readily removed but which will retain substantial strength after removal of the panel.

The foregoing problems have been especially acute in the labeling of articles intended for retail sale. It is sometimes desirable to use a removable panel on a label for such goods. If the panel is difficult to remove, of if the label is so weakened by removal of the panel that it breaks in an unintended manner, then the purchaser may be dissatisified with the goods.

SUMMARY OF THE INVENTION

It is an object of the present invention to provide a label which has a panel that can readily and nearly be removed but which will retain substantial strength after removal of the panel.

It is a further object of the present invention to provide a labeled article which incorporates such a label and which has the desirable attributes referred to above.

A label in accordance with the present invention is sheet like and includes a pattern of plural tear lines. The tear lines define a panel and an elongated strip. A first edge of the panel is contiguous with the strip. The tear lines extend around the periphery of the panel and along both sides of the strip. Thus, one of the tear lines defines the boundary between the panel and the strip. The label also includes means for providing digital access to a first end portion of the strip for initiating separation of such end portion from the remainder of the label.

The strip may be removed from the label by grasping the first end of the strip and pulling it. This action frees the first edge of the panel, which was formerly contiguous with the strip. The first edge of the panel may be readily grasped and the panel may be pulled away from the remainder of the label. Because the remainder of the label completely surrounds the panel and the strip, the edges of the label will remain continuous after the strip and panel have been removed, and the label will therefore retain substantial strength after such removal.

The labeled article of the present invention includes a label of the type described above secured to the body of the article so that the label closely overlies a surface of such body. The panel can be removed from the label and from the article in the manner described above. In a preferred embodiment, the label is secured to the body only at its ends, which are remote from the panel and the strip. Because the label retains substantial strength after removal of the panel, the portions of the label remote from the ends will remain in close overlying engagement with the body after such removal.

The removable panel of the label may serve as an "in-store" discount coupon. The panel is printed with indicia of a discount to be allowed by the retailer on purchase of the article and to be repaid by the manufacturer to the retailer upon presentation of the panel or coupon. Because the panel of the label can be removed readily and neatly from the article by the retail customer, and because the panel is formed integrally with the label of the article at no additional cost, the present invention provides a practical structure for distributing a discount coupon along with an article intended for retail sale. When this structure is utilized, the retailer can only obtain the discount coupons by purchasing the articles at wholesale and the problem of fraudulent coupon redemption by retailers is obviated.

Other objects, features and advantages of the present invention will be more readily apparent from the detailed description of the preferred embodiments set forth below when read in conjunction with the accompanying drawings, in which like reference numerals are used to denote like features in the various views.

DETAILED DESCRIPTION OF THE PREFERRED EMBODIMENTS

Figure 1:
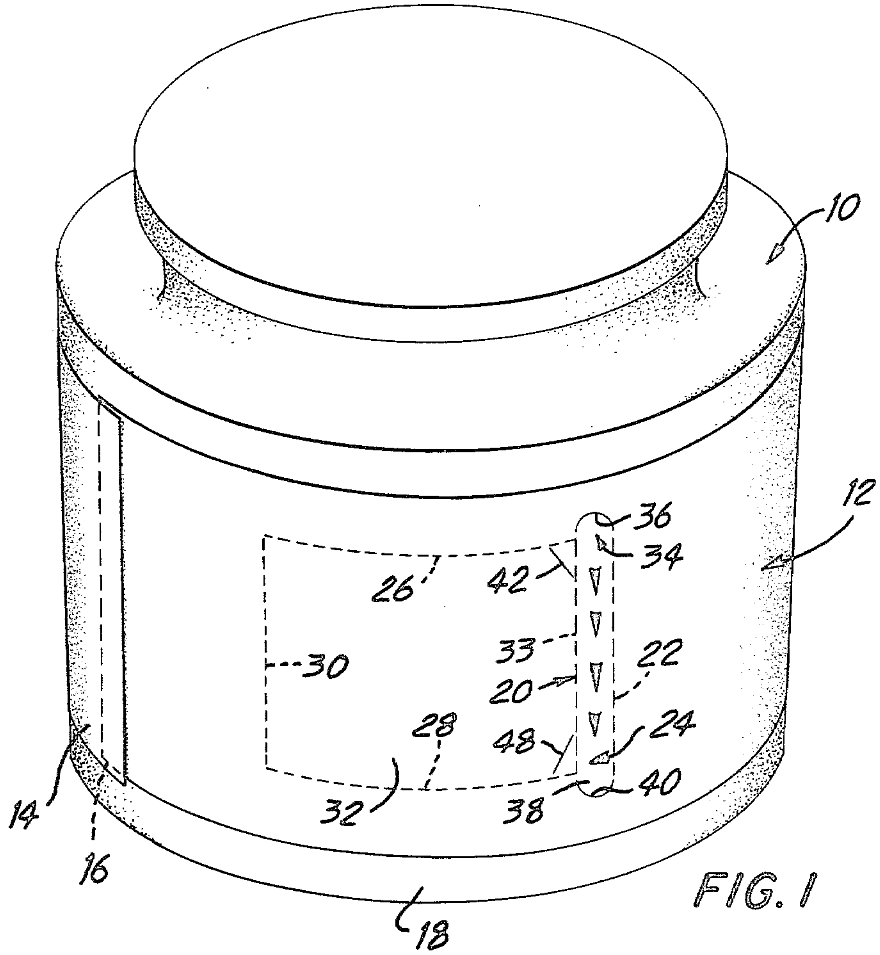
FIG. 1 is a perspective view of a labeled article in accordance with the preferred embodiment of the present invention.

As shown in FIG. 1, a labeled article according to the preferred embodiment of the present invention includes a body 10, such as a jar or other container, and a label 12. The label is elongated and extends around the body so that one end 14 of the label overlaps the opposite end 16 of the label. The underlying end 16 is secured to the body by an adhesive (not shown). The overlying end 14 is secured to the underlying end 16, and thus to the body 10, by a further adhesive (not shown). This arrangement maintains the label 12 in close overlying relation with the generally cylindrical surface 18 of the body.

The label 12 is formed from a single sheet of paper and includes two tear lines 20 and 22 which extend generally parallel with one another and which thus define an elongated strip 24 between them. One of these tear lines 20 forms a first long side of the strip and the other one of these tear lines 22 forms the second long side of the strip. The strip 24 extends axially with respect to the cylindrical body surface 18.

The label also includes additional tear lines 26, 28 and 30. These additional tear lines, together with a portion of the first-mentioned tear line 20, cooperatively define a generally rectangular panel 32 which is contiguous with the strip 24. The portion of tear line 20 which forms the boundary between the panel 32 and the strip 24 also defines a first edge 33 of the panel 32. The tear lines 26 and 28 which respectively form the second and third edges of the panel 32 extend generally perpendicularly to the tear line 20 and intersect it.

The tear line 30 which forms the fourth edge of the panel 32 extends generally parallel to the first side of the strip and intersects the tear lines 26 and 28. Thus, the tear lines which define the panel extend around its entire periphery. Each of the aforementioned tear lines consists of a row of spaced perforations.

Figure 5:
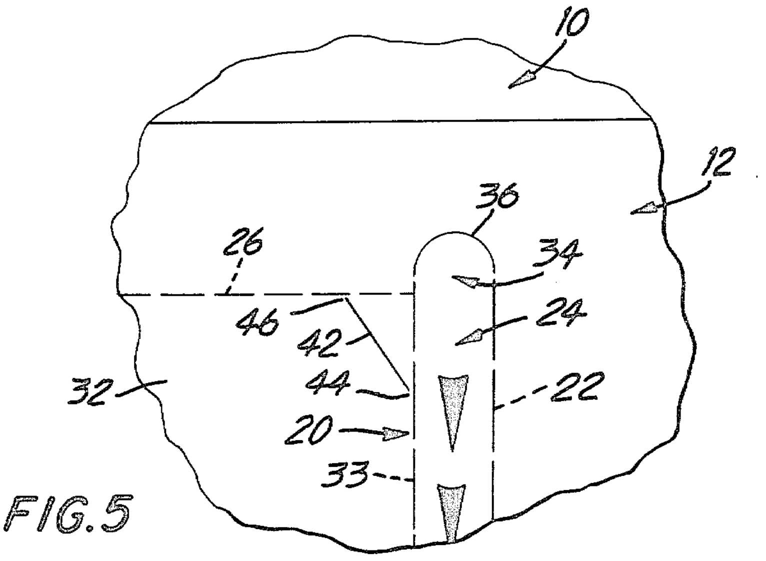
FIG. 5 is a fragmentary elevational view, on an enlarged scale, depicting a portion of the article shown in FIG. 1.

As best seen in FIG. 5, a first end 34 of the strip 24 extends beyond the second edge 26 of the panel. A generally arcuate cut 36 extends across the strip at its first end 34. This cut is generally convex in the direction away from the strip (towards the top of FIG. 5). In a similar fashion, a second end 38 of the strip 24 (FIG. 1) extends beyond the third edge 28 of the panel. A second arcuate cut 40 extends across the strip at its second end 38, and is generally convex in the direction away from the strip (towards the bottom of FIG. 1).

As shown in FIG. 5, a skew cut 42 extends across the corner defined by the first edge 33 and the second edge 26 of the panel. The skew cut extends obliquely of the first edge 33 of the panel. A first end 44 of the skew cut is immediately adjacent to the first edge 33 of the panel. The second end 46 of the skew cut is immediately adjacent to the second edge 26 of the panel. Two features of a label are "immediately adjacent", as the term is used in this disclosure, when they are contiguous or are within about 1/16 of an inch from one another. The skew cut does not extend beyond the edges of the panel.

A second skew cut 48 (FIG. 2) extends obliquely of the first edge 33 of the panel across the corner defined by the first edge 33 and the third edge 28 of the panel. One end of the second skew cut 48 is immediately adjacent to the first edge 33 of the panel and the opposite end of the second skew cut 48 is immediately adjacent to the third edge 28 of the panel. The second skew cut does not extend beyond the edge of the panel.

The exposed surface of the label 12 has printed indicia on it which indicate the procedure by which the panel can be removed from the label. These indicia include a row of the arrowheads along the strip 24. Of course, the other indicia (not shown) may be printed on the label. These may include indicia indicative of a discount printed on the panel 32, so that the panel 32 can serve as a discount coupon for presentation upon purchase of the article in a retail store.

The sequence of operations used to remove the panel from the label and from the article can best be appreciated with reference to FIGS. 1 through 4 in sequence. The user of the article first engages the first end 34 of the strip 24 with his hand. Digital access for such engagement is provided by the first arcuate cut 36; by scraping a fingernail downwardly across the surface of the label, the user can get his fingernail into the first arcuate cut 36 and thus engage the first end 34 of the strip. The body 10 of the labeled article assists in this process by supporting the surrounding portions of the label 12.

Figure 2:
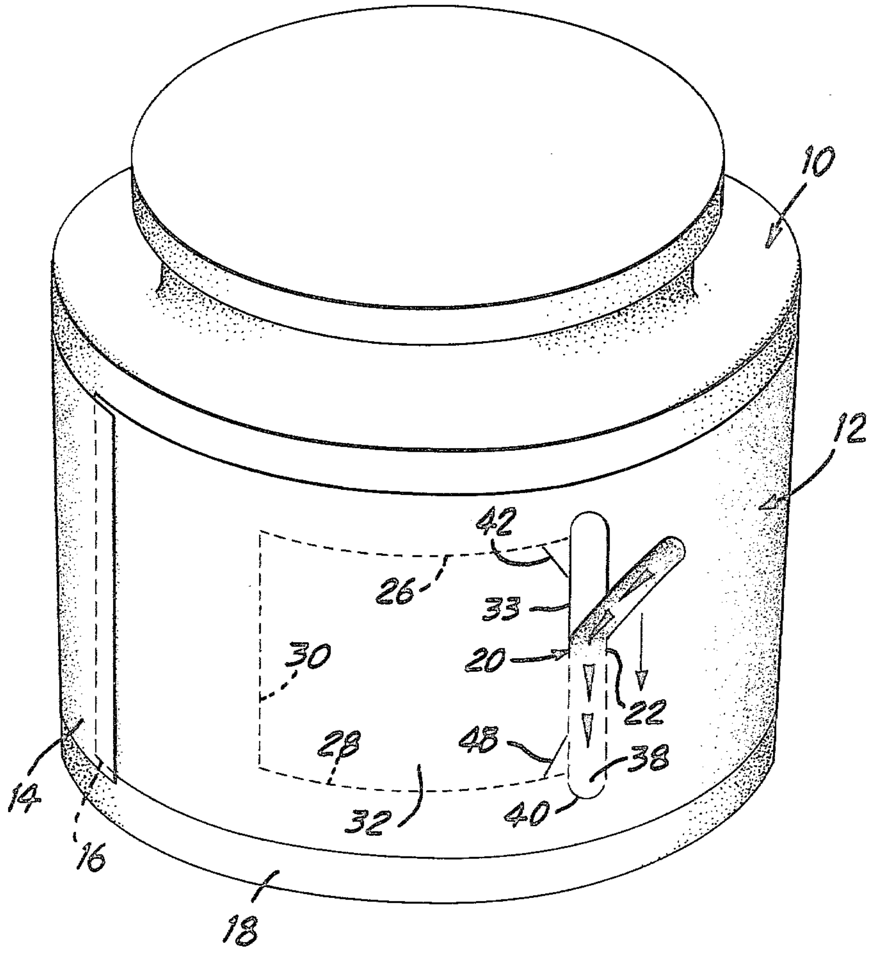
FIGS. 2 and 3 are views similar to FIG. 1 depicting the article shown in FIG. 1 during successive stages in the strip and panel removal process.
Figure 3:
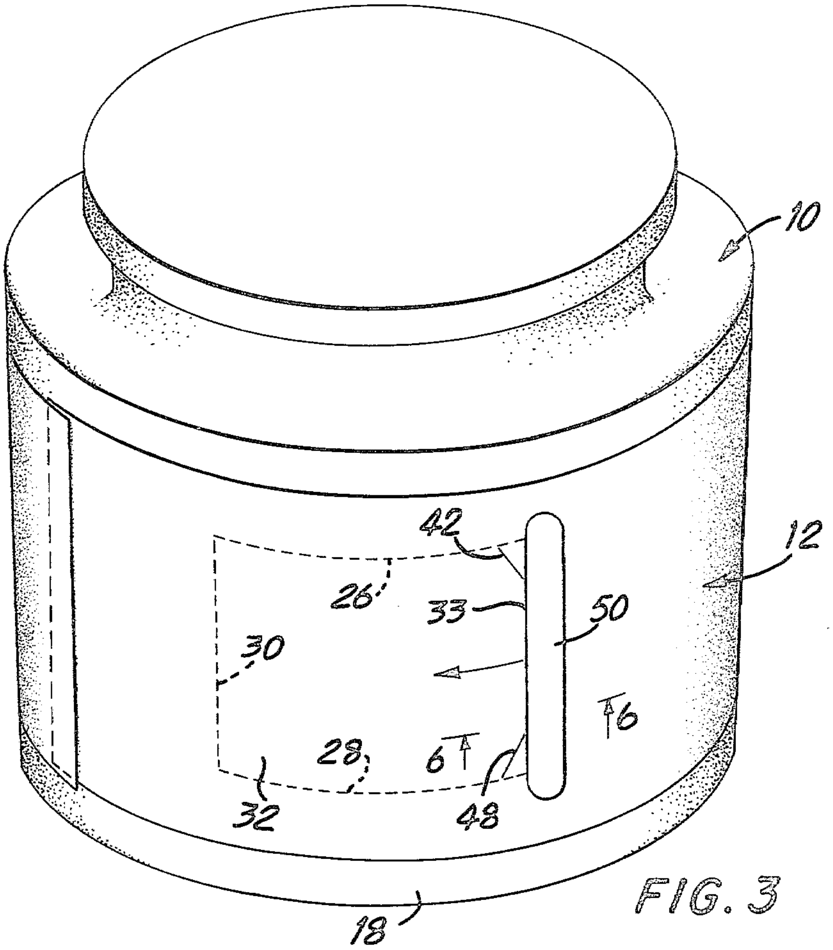

Once the user has engaged the first end 34 of the strip, he can pull it longitudinally as shown in FIG. 2 to part the strip from the remainder of the label along the tear lines 20 and 22. An undesirable randomly oriented tear extending through a portion of the panel may be started during this operation at the intersection of the tear lines 26 and 20. However, the first skew cut 42 will arrest any such randomly oriented tear.

As the user continues to pull the strip, he will eventually reach the second end 38 of the strip. At this point, the strip 24 will be entirely freed from the remainder of the label and from the article; the user may simply discard the strip.

Figure 6:
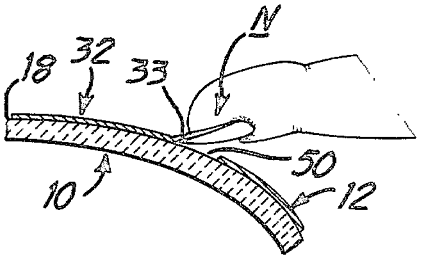
FIG. 6 is a fragmentary sectional view taken along line 6—6 in FIG. 3.
Figure 4:
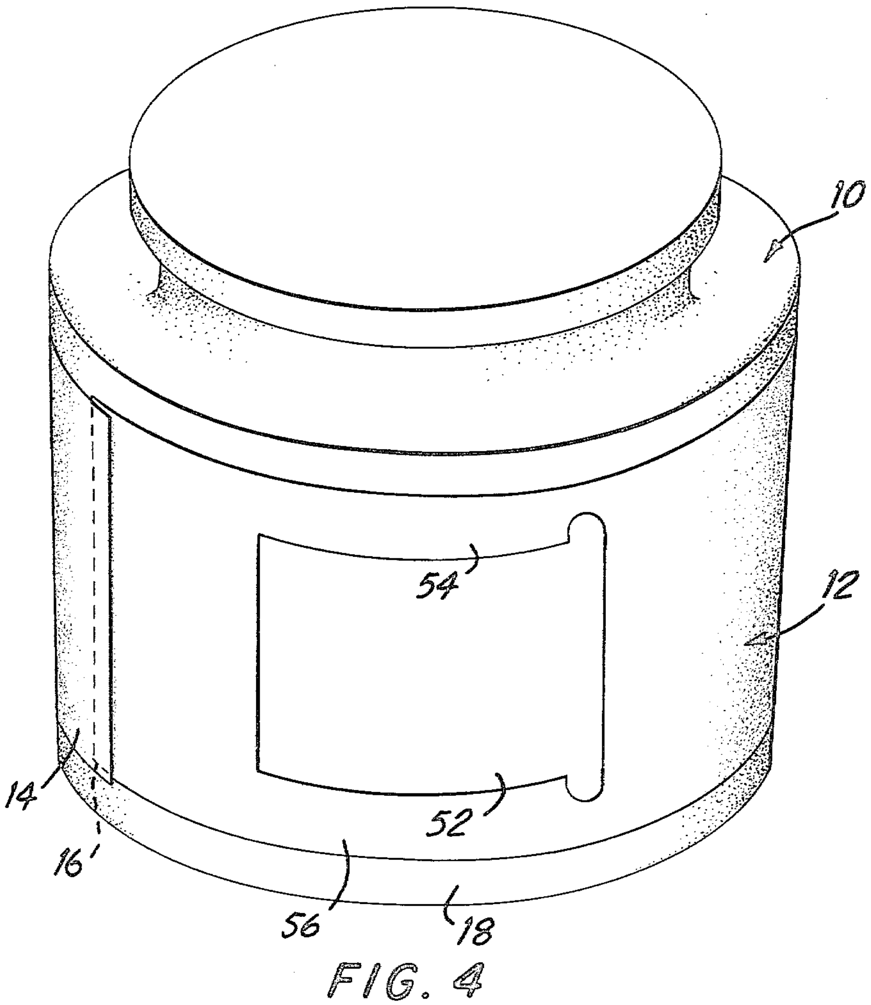
FIG. 4 is a view similar to FIG. 1 showing the article depicted in FIG. 1 after removal of the strip and panel.

Once the strip has been removed, the first edge 33 of the panel is freed from any surrounding portions of the label and a slot 50 (FIG. 3) is provided immediately adjacent to the first edge of the panel in the area formerly occupied by the strip. Because the slot 50 extends generally axially on the cylindrical surface 18 of the body, the first edge 33 of the panel is elevated somewhat above the opposite edge of the slot 50 as shown in FIG. 6. The user may readily insert a fingernail N beneath the first edge 33 of the panel to engage the panel.

Because of the skew cuts 42 and 48 at the corners of the panel, the first edge 33 of the panel may be lifted slightly away from the body without tearing the portions of tear lines 26 and 28 adjacent to the slot 50. Thus, the user can readily start to lift the first edge 33 with his fingernail without initiating any randomly-oriented tears in the panel. Once the first edge 33 has been lifted slightly, the user can readily grasp the adjacent portion of the panel 32 between his thumb and forefinger and he can peel the panel away from the body in the direction indicated by the arrow in FIG. 3. This action parts the label along the tear lines 26 and 28. Because the user can grasp the panel firmly before parting the label along the tear lines 26 and 28, he can easily control the direction of the forces applied to the panel during this process to part the label neatly along these tear lines.

Because the strip 24 originally extended beyond the second edge 26 and the third edge 28 of the panel, the slot 50 formed upon removal of the strip also extends beyond the second and third edges of the panel. Such extension of the slot helps to prevent the initiation of random tears as the user parts the label along the tear lines 26 and 28 which define the second and third edges of the panel.

After the label has been completely parted along the tear lines 26 and 28, the user can then readily part the panel from the remainder of the label along the single remaining tear line 30.

After the strip and panel have been removed from the label, a hole 52 (FIG. 4) is left in the label in the area formerly occupied by the strip and panel. Because the strip and the panel were completely surrounded by the remainder of the label 12, a pair of "bridges" 54 and 56 remain at the edges of the label adjacent to the hole 52. Thus, even after removal of the strip and panel, the edges of the label still extend continuously between the ends 14 and 16 of the label. Although the label is only secured to the container 10 at the ends 14 and 16, the portions of the label remote from such ends will still be held closely against the surface of the body after removal of the panel and strip.

The material utilized for the label of the present invention will depend on the application. If the article is a consumer product, paper is preferred.

It is generally preferable to make the strip between about $\frac{1}{8}$ inch and $\frac{1}{4}$ inch wide, and a width of approximately 3/16 inch is especially preferred. Preferably, the perforations which constitute the tear lines 20 and 22 along the long sides of the strip 24 are substantially uniform and have a pitch or distance between corresponding features of adjacent perforations of about $\frac{1}{8}$ inch. The perforations which constitute the tear lines defining the second edge 26, third edge 28 and fourth edge 30 of the panel 32 are preferably also substantially uniform but have a pitch of about 1/16 inch. The first end 34 of the strip preferably extends beyond the second edge 26 of the panel by about ⅛ inch as measured on the center of the strip. The arcuate cut 36 preferably intersects the edges of the strip 24 at equal angles of not more than about 70°. The features of the strip at its second end 38 are preferably similar to those at its first end 36.

The first end 44 (FIG. 5) of the first skew cut 42 is preferably spaced from the second edge 26 of the panel by between about ⅛ inch and about ¼ inch as measured along the first edge 33 of the panel. Also, the second end 46 of the skew cut is preferably spaced from the first edge 33 of the panel by between about ⅛ inch and ¼ inch as measured along the second edge 26 of the panel. The second skew cut 48 (FIG. 1) is preferably identical to the first skew cut, so that both of them are substantially straight and continuous and they define equal but opposite angles with the first edge 33 of the panel. Each such angle is preferably between about 30° and 70°.

In an alternate embodiment of the present invention the strip 24 is omitted from the label. The area occupied by the strip in the embodiment described above is cut out of the label during manufacture to provide a slot in the label contiguous with the first edge of the panel. Thus, the label and labelled article of this alternate embodiment have the configurations shown in FIG. 3; the slot in the label extends beyond the second and third edges of the panel. Preferably, the label according to this alternate embodiment of the present invention incorporates the skew cuts described above. If the body of the labelled article has a cylindrical surface, the slot preferably extends axially with respect to such surface. The panel can be removed from a labelled article in accordance with this alternate embodiment by using a sequence of steps exactly the same as the sequence of removal steps described above, but omitting the strip removal steps.

Numerous variations and combinations of the features described above may be utilized without departing from the spirit of the present invention. Merely by way of example, the label of the present invention can be applied to a body having flat surfaces and can be applied to a body having a cylindrical surface in such a manner that the strip extends generally circumferentially along such surface. Therefore, the foregoing description should be considered merely illustrative and should not be taken as limiting the scope of the present invention as defined in the appended claims

What is claimed is:

1. An article comprising:
(a) a body;
(b) a sheet like label secured to said body and closely overlying a surface thereof, said label having a pattern of plural tear lines which define a panel and an elongated strip, said panel and said strip being integral parts of the label, a first edge of said panel being contiguous with a first long side of said strip, said tear lines extending around the periphery of said panel and along the long sides of said strip, one of said tear lines defining the boundary between said panel and said strip, the remainder of said label completely surrounding said panel and said strip; and
(c) means for providing digital access to a first end portion of said strip for initiating separation of such end portion from the remainder of said label.

2. An article as claimed in claim 1 in which said label is secured to said body only at portions of said label remote from said panel and said strip.

3. An article as claimed in claim 1 in which said digital access means includes an arcuate cut extending across said strip at a first end thereof.

4. An article as claimed in claim 1 in which the surface of said body which said label overlies is generally cylindrical and said strip extends axially with respect to such surface.

5. An article as claimed in claim 1 or claim 3 in which a second edge of said panel angularly intersects the first edge of said panel and the first end of said strip extends beyond the second edge of said panel.

6. An article as claimed in claim 5 in which said label is a sheet of paper and each one of said tear lines is a row of spaced perforations.

7. An article as claimed in claim 5 in which said label has a skew cut which extends obliquely of said first edge across the corner of said panel defined by the first and second edges thereof.

8. An article as claimed in claim 7 in which a third edge of said panel angularly intersects the first edge of said panel and the second end of said strip extends beyond such third edge.

9. An article as claimed in claim 8 in which said label has a second skew cut which extends across the corner of said panel defined by said first and third edges thereof.

10. An article as claimed in claim 1, further comprising indicia indicative of the procedure for removal of the panel on the exposed surface of the label.

* * * * *

UNITED STATES PATENT AND TRADEMARK OFFICE

CERTIFICATE OF CORRECTION

PATENT NO. : 4,318,235

DATED : March 9, 1982

INVENTOR(S) : Joseph L. Augeri

It is certified that error appears in the above—identified patent and that said Letters Patent is hereby corrected as shown below:

Column 1, line 34, "nearly" should read --neatly--.

Column 1, line 27, "of" should read --or--.

Signed and Sealed this

*Twenty-fifth* Day of *May 1982*

[SEAL]

*Attest:*

GERALD J. MOSSINGHOFF

*Attesting Officer* *Commissioner of Patents and Trademarks*